(12) United States Patent
Hasenzahl

(10) Patent No.: US 8,845,197 B2
(45) Date of Patent: Sep. 30, 2014

(54) DENTAL MACHINING UNIT WITH TOOL SPINDLE

(75) Inventor: Thomas Hasenzahl, Darmstadt (DE)

(73) Assignee: Sirona Dental Systems GmbH, Bensheim (DE)

( * ) Notice: Subject to any disclaimer, the term of this patent is extended or adjusted under 35 U.S.C. 154(b) by 710 days.

(21) Appl. No.: 12/010,791

(22) Filed: Jan. 30, 2008

(65) Prior Publication Data

US 2008/0226409 A1 Sep. 18, 2008

Related U.S. Application Data

(60) Provisional application No. 60/906,523, filed on Mar. 13, 2007.

(30) Foreign Application Priority Data

Mar. 13, 2007 (DE) .......................... 10 2007 012 586

(51) Int. Cl.
| | |
|---|---|
| *A61C 1/10* | (2006.01) |
| *F16C 41/04* | (2006.01) |
| *G01L 5/00* | (2006.01) |
| *G01L 1/22* | (2006.01) |
| *A61C 1/00* | (2006.01) |
| *A61C 19/04* | (2006.01) |
| *A61C 1/18* | (2006.01) |
| *A61B 17/16* | (2006.01) |
| *A61B 17/00* | (2006.01) |
| *A61B 19/00* | (2006.01) |

(52) U.S. Cl.
CPC . *A61C 1/00* (2013.01); *A61C 19/04* (2013.01); *A61C 1/185* (2013.01); *G01L 5/0019* (2013.01); *A61B 17/1626* (2013.01); *A61B 2017/00017* (2013.01); *G01L 1/2231* (2013.01); *A61B 2019/464* (2013.01); *A61B 19/46* (2013.01)
USPC .......................................... 384/448; 433/114

(58) Field of Classification Search
USPC ......... 384/448; 73/862.637, 862.49, 862.636, 73/862.325, 862.321; 433/114–133
See application file for complete search history.

(56) References Cited

U.S. PATENT DOCUMENTS

| | | | | |
|---|---|---|---|---|
| 2,681,565 | A * | 6/1954 | Kelk ........................... | 73/862.49 |
| 3,124,770 | A * | 3/1964 | Ciavatta ............................ | 338/5 |
| 3,418,715 | A * | 12/1968 | Ellis ................................ | 433/126 |
| 4,168,160 | A * | 9/1979 | Stoferle et al. ............. | 73/862.49 |

(Continued)

FOREIGN PATENT DOCUMENTS

| | | | | |
|---|---|---|---|---|
| DE | 10206679 | C1 * | 8/2003 | ............... G01L 5/12 |
| JP | 59163531 | A * | 9/1984 | ................ G01L 5/12 |

OTHER PUBLICATIONS

Machine Translation of DE 10206679. Feb. 18, 2002.*

*Primary Examiner* — Alan B Waits
(74) *Attorney, Agent, or Firm* — Fitzpatrick, Cella, Harper & Scinto

(57) ABSTRACT

The present invention relates to dental machining apparatus (1) for blanks (3) comprising a tool spindle (2) having an axis of rotation (2.8) and mounted in a bearing housing (1.2) disposed on the machine housing side. A force sensor (5) is also provided, which is disposed between the tool spindle (2) and the bearing housing (1.2) for the purpose of detecting the machining force acting on the tool spindle (2), wherein the tool spindle (2) can be supported against the bearing housing (1.2) directly or indirectly via the force sensor (5).

22 Claims, 5 Drawing Sheets

(56) References Cited

U.S. PATENT DOCUMENTS

| | | | | |
|---|---|---|---|---|
| 4,419,901 A | * | 12/1983 | Ruppert et al. | 73/862.49 |
| 5,677,488 A | * | 10/1997 | Monahan et al. | 73/593 |
| 5,905,212 A | * | 5/1999 | Moses et al. | 73/862.451 |
| 6,324,919 B1 | * | 12/2001 | Larsen et al. | 73/862.043 |
| 6,360,616 B1 | * | 3/2002 | Halliday et al. | 73/862.49 |
| 6,546,790 B1 | * | 4/2003 | Halliday | 73/146 |
| 7,497,131 B2 | * | 3/2009 | Sentoku | 73/862.322 |
| 2006/0120819 A1 | | 6/2006 | Honegger et al. | |

\* cited by examiner

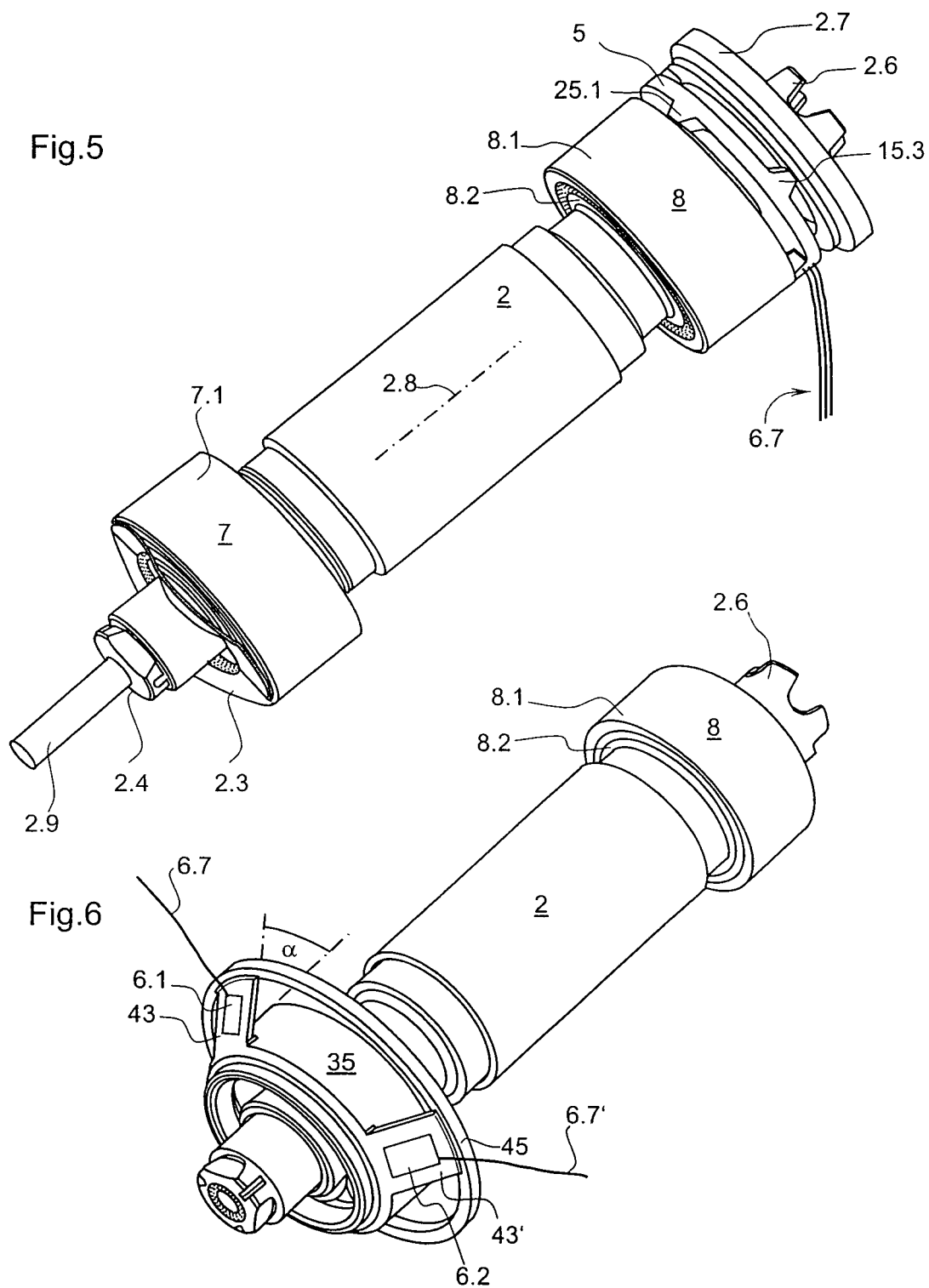

DENTAL MACHINING UNIT WITH TOOL SPINDLE

TECHNICAL FIELD

The invention relates to dental machining apparatus with a tool spindle having an axis of rotation and a bearing housing to hold the tool spindle and shaft respectively, including shaft bearings.

DESCRIPTION OF THE PRIOR ART

In dental machining apparatus known hitherto, the machining or cutting force of the tool is determined indirectly via the current uptake of the motors. Due to the time difference existing between the occurrence of a change in the cutting or grinding force generated on the tool and the subsequent change in current, a dead time occurs during measurement processes, resulting in inaccuracy.

It is an object of the invention to design and arrange a dental machining apparatus with a tool spindle such that optimal detection of the forces acting on the tool is assured.

SUMMARY OF THE INVENTION

The problem is solved by the invention by providing a force sensor disposed between the tool spindle and the bearing housing so as to record the machining force acting on the tool spindle, this being supported against the bearing housing directly or indirectly via the force sensor. No provision is made for any relative movements between the force sensor and the tool spindle on the one hand and between the force sensor and the bearing housing on the other whilst neglecting the elasticities, existing at least on the sensor side, and the associated deformation.

The result of this is that all forces absorbed by the tool and the spindle which are transmitted through the bearing housing to the spindle holder, can be detected by the force sensor. Thus detection of the cutting or machining force on the tool is accomplished independently of a motor driving the spindle and thus independently of the current drawn by the motor.

It is advantageous if the force sensor has at least one sensor element in the form of a measuring bridge or a piezo element, in which case the measuring bridge is designed using thick film technology or as a strain-gage element. The use of a strain-gage measuring bridge represents the most commonly used option for equipping the force sensor. The arrangement of the strain-gage element or the piezo element on the force sensor and its positioning thereon depend on the structure of the force sensor on the one hand and on the force it is desired to determine on the other. The measuring bridge may be designed as a full bridge or also as a half bridge or quarter bridge. When a full bridge is used, the effects due to temperature fluctuations are weaker.

It is also advantageous if the force sensor is designed as an axial force sensor in the form of a circular disk having at least a center axis, a first flat face and an opposing second flat face and which can be caused to bear against the bearing housing and the tool spindle and its bearing in the axial direction relative to the axis of rotation. Depending on the tool used, sensing of the axial force is of particular importance. The force sensor is in the form of a circular disk, which also forms the axial bearing of the spindle, assuring extensive absorption of the machining forces arising in the axial direction.

It is also of advantage if the respective flat face displays several bracing members and the bracing members of the first flat face are offset from the bracing members on the second flat face in the circumferential direction in such a way that a load on the bracing members in the axial direction leads to a bending load on the circular disk, wherein the sensor element is preferably designed as a strain-gage full bridge with four resistance meanders and disposed on the circular disk in the deformation zone. The bracing members on each face are offset from each other by 120, the offset between the bracing members on the first flat face and the bracing members on the second flat face being 60, so that besides achieving stability of positioning of the force sensor, maximal deformation of the same is assured.

It is also advantageous if the bracing member has a basically semicircular, arcuate or trapezoidal shape. The design of the bracing members depends on the desired deformation in the region of the respective strain-gage element of the force sensor.

In this connection it is advantageous if the bracing member has a bracing surface facing an axial direction for the purpose of forming a flat or pointed contact surface.

Pointed bracing surfaces assure, in particular with respect to the respective three bracing surfaces, maximal steadiness of the position of the force sensor, so that tipping of the respective bracing surface is excluded.

It is also of advantage if at least three bracing members are provided on the first flat face and at least three on the second flat face. The mounting position of the respective flat face of the force sensor is thereby stabilized.

It is also advantageous if the spindle has a rotary bearing with a race ring and if at least the bracing members on the first flat face can be caused to bear against the race ring on the tool spindle and that at least the bracing members on the second flat face can be caused to bear against the bearing housing. The force is transmitted from the tool through the chuck system on the spindle side and the spindle shaft to the inner race of the bearing, and thence through the rolling element of the bearing to the outer race of the bearing and thence to the force sensor. From the force sensor the introduced cutting force is transmitted through the bearing housing to the spindle holder on the machine side. The outer race ring has not been moved radially so that the position of the force sensor thereon is stabilized.

The object of the invention is further achieved in that the force sensor has a center axis, an annular carrier for holding the tool spindle and an annular bearing disposed coaxially therewith for mounting the same in the bearing housing, wherein the carrier and the bearing are connected to each other by a plurality of bracing members in such a way that the load on the carrier in the radial and axial directions leads to deformation of the bracing members, and at least one bracing member has a sensor element. As a result of this, both axial and radial cutting forces introduced into the spindle via the tool are detectable by a force sensor. The connection between the carrier and the bearing is created exclusively via the bracing members so that any force introduced into the carrier is transmitted to the bearing via the bracing members and is thus fully detectable.

In this context it is of advantage if three bracing members are uniformly distributed along the circumference. A result of the use of three bracing members distributed uniformly over the circumference is that, in particular, detection of forces generated in the radial direction in terms of magnitude and direction is assured.

It is further of advantage if the bracing member is designed as a flat bracing member having a rectangular cross-section. The flat, rectangular design variant assures the necessary stability for transmission of the spindle forces to the bearing housing. In addition, adequate flexibility of the respective bracing members is given with regard to the sensor members disposed thereon and deformation thereof for the purpose of detecting said forces.

It is also of advantage if each bracing member encloses an angle α of between 0° and 90°, especially between 30° and 60° with the center axis. The choice of the value of α governs the ratio of the deformation of the bracing members resulting from axial forces to the deformation of the bracing members resulting from radial forces. The value of α is selected in accordance with the type and size of the tool used.

It is further of advantage if the spindle comprises a rotary bearing with a race ring, wherein the bearing can be caused to bear against the race ring with a friction fit or form fit, and the carrier can be caused to bear against the bearing housing by a friction or form fit. Since the force sensor transmits the forces introduced through the spindle and rotary bearing to the bearing housing and is intended to sense these forces in their entirety, a rigid connection is required, in this respect, between the race ring and the bearing on the one hand and between the carrier and the bearing housing on the other. This rigid connection may be provided with the aid of various conventional fixing means such as shrink fitting, screws, or clips.

BRIEF DESCRIPTION OF THE DRAWINGS

The method of the invention is explained with reference to the following drawings, in which:

FIG. 5 is a schematic illustration of the spindle showing the bearings and the axial force sensor;

FIG. 6 is a schematic illustration of the spindle comprising the bearing and a combined axial/radial force detector;

DESCRIPTION OF EXEMPLARY EMBODIMENTS OF THE INVENTION

Figure 1:
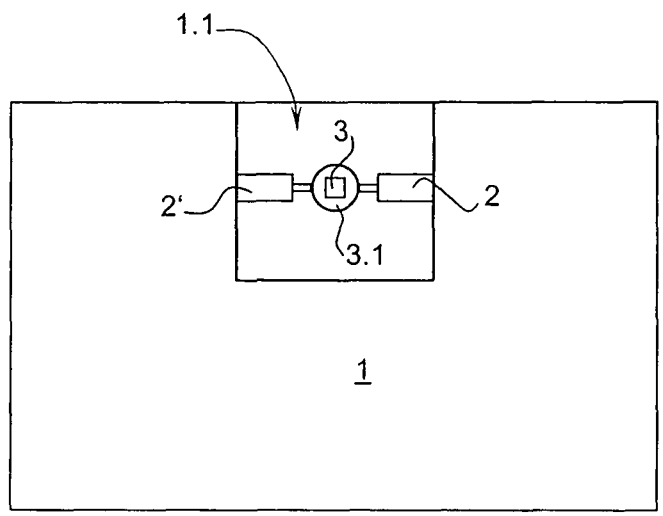
FIG. 1 is a schematic representation of dental machining apparatus comprising a machining chamber and spindle.
Figure 2:
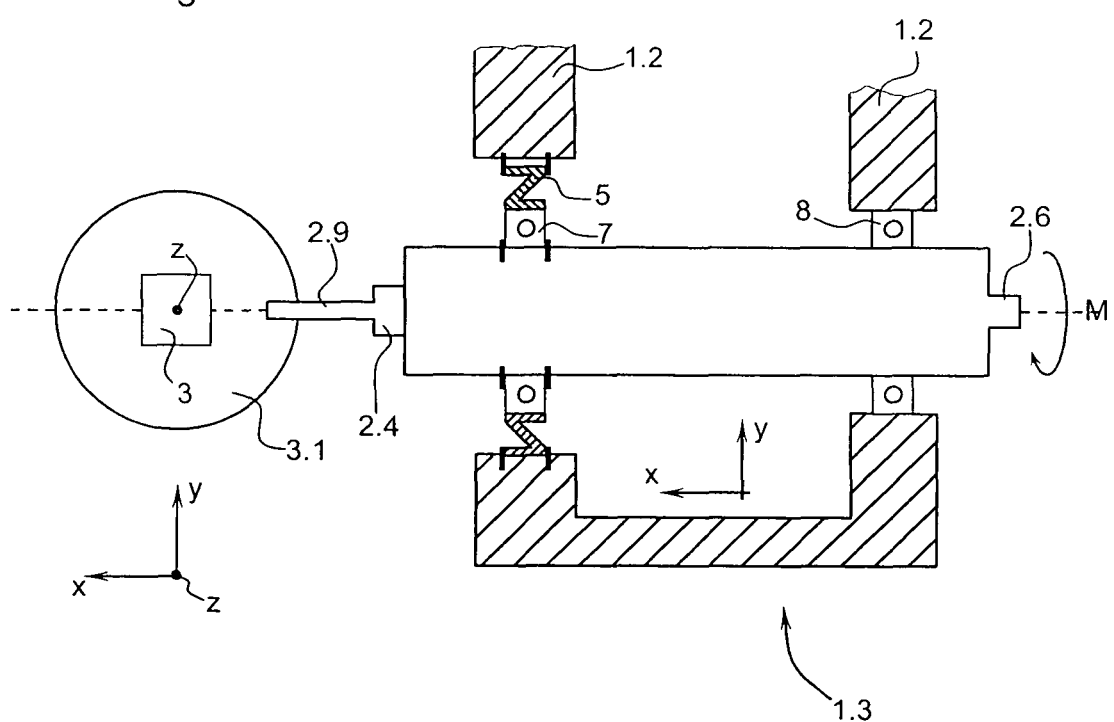
FIG. 2 is a schematic representation of the bearings of the spindle inside the dental machining apparatus.

FIG. 2 is a schematic representation of the bearings of a tool spindle 2 of dental machining apparatus 1 as shown in FIG. 1. The tool spindle 2 has a chuck system 2.4 at its end facing a workpiece 3 to accommodate a tool 2.9 which extends into the machining chamber 1.1.

The tool spindle 2 is held in a spindle holder 1.3 of the machining apparatus 1 via a bearing housing 1.2. The spindle holder 1.3 holding the tool spindle 2 can be moved together with the tool 2.9 in a direction X toward the workpiece 3 and away from it and can also be moved in the direction Y transversely to the tool 2.5. This is indicated by the arrows in the X and Y directions. The workpiece 3 is held in a workpiece holder 3.1 that can be driven in the direction Z.

The tool spindle 2 is mounted on the housing side in a bearing housing 1.2 substantially immovably axially and radially in order to perform very precise machining operations on the workpiece 3.

The tool spindle 2 is driven by a motor M, not shown, and is supported in the bearing housing 1.2 by bearings 7, 8. For direct measurement of the machining forces occurring during the machining process in the axial and/or radial directions, a force sensor 5 is disposed between the bearing 7 and the corresponding bearing position in the bearing housing 1.2.

In FIGS. 3 to 6 the force sensor 5 itself, on the one hand, and the arrangement of the force sensor 5, on the other, are shown in detail.

Figure 3:
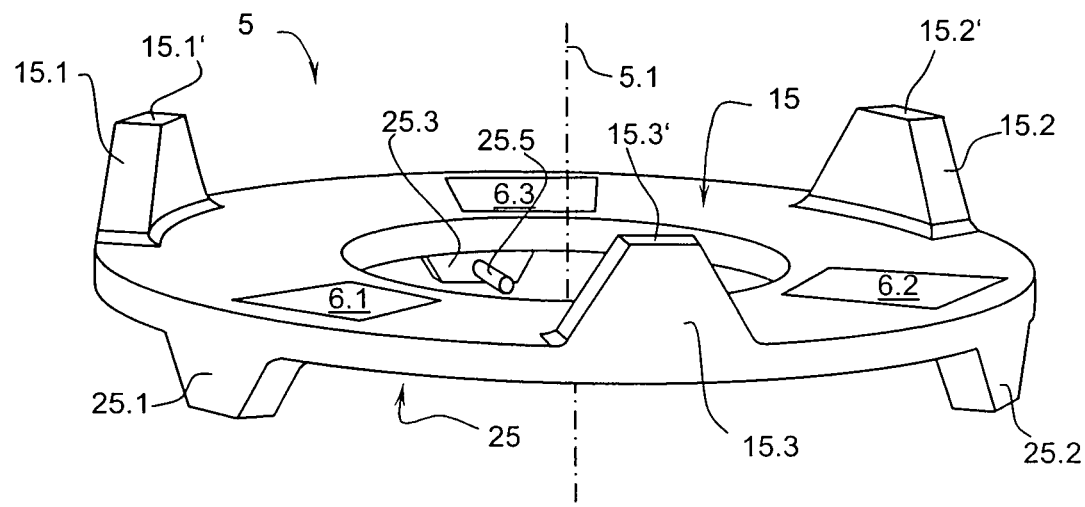
FIG. 3 is a schematic illustration of the axial force sensor.

The force sensor 5 shown in FIG. 3 for detecting an axial force is essentially in the form of a circular disk which displays on its first flat side three bracing members 15.1 to 15.3 and on its second flat side 25 three bracing members 25.1 to 25.3. The bracing members 15.1 to 15.3 and 25.1 to 25.3 are distributed around the circumference relative to the center axis 5.1 on the outer edge of the force sensor 5, each being offset relatively to the neighboring bracing members by 120°. The bracing members 15.1 to 15.3 on the first flat side 15 are each offset from the bracing members 25.1 to 25.3 on the second flat side by 60°. On the first flat side 15 two sensor members 6.1, 6.2 are provided, the respective sensor members 6.1, 6.2 being positioned between two bracing members 15.3 and 15.1 or 15.3 and 5.2 respectively in the region of the deformation zone of the partial sector of the circle. Each of the sensor members 6.1, 6.2 on the first flat side 15 is thus also disposed laterally relative to the respective bracing members 25.1, 25.2 on the second side 25.

Figure 7:
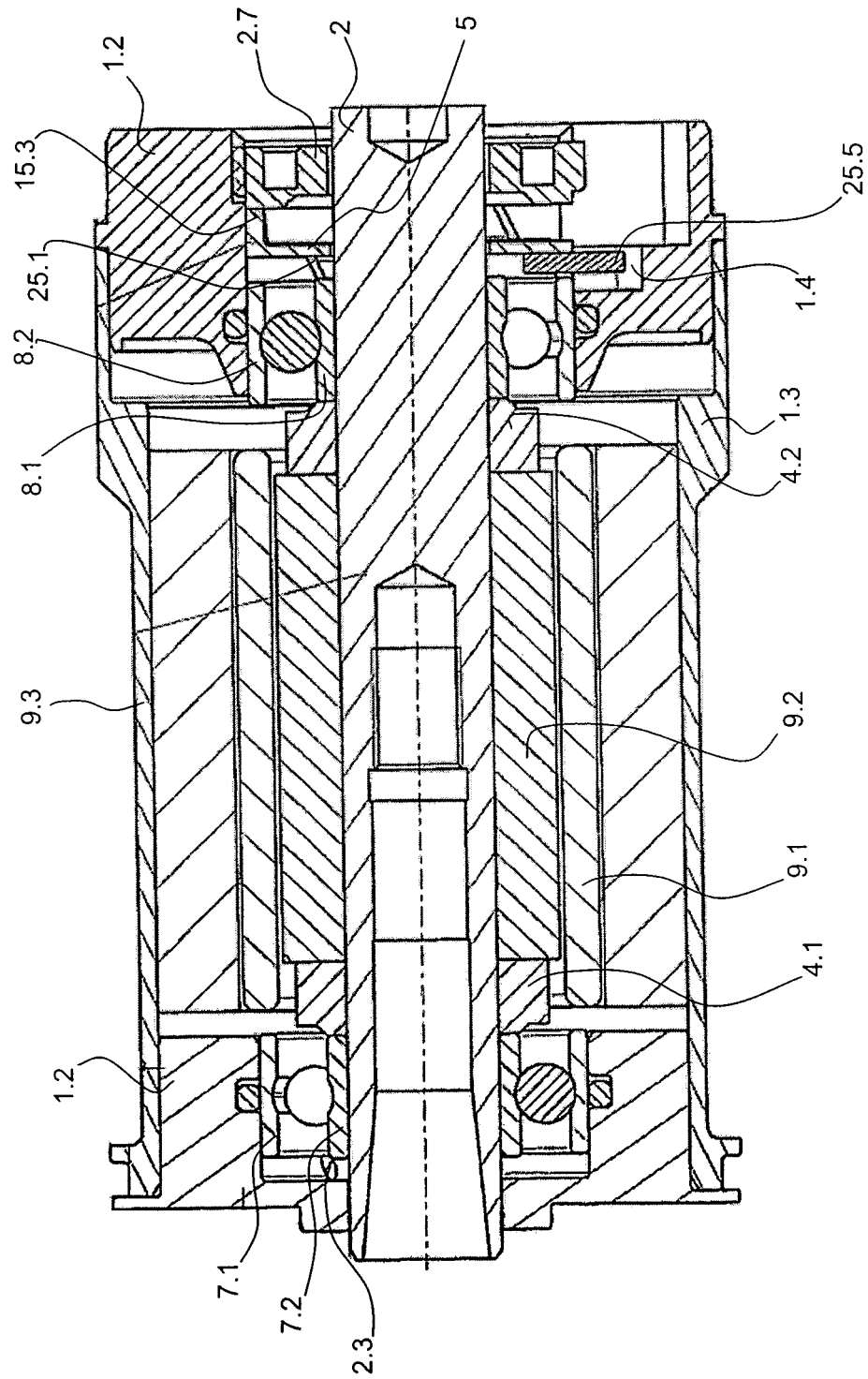
FIG. 7 is a cross-section of the tool spindle with integrated motor.

The bracing members 25.3 has an anti-rotation element in the form of a pin 25.5 oriented in the radial direction toward the bracing members 25.3, and as shown in FIG. 7, projects in the radial direction beyond the force sensor in the form of a circular disk. The pin 25.5, as FIG. 7 shows, engages a recess 1.4 in the bearing housing 1.2.

Each of the bracing members 15.1 to 25.3 has a basically trapezoidal shape and a rectangular contact surface 15.1' to 15.3' respectively.

Figure 4:
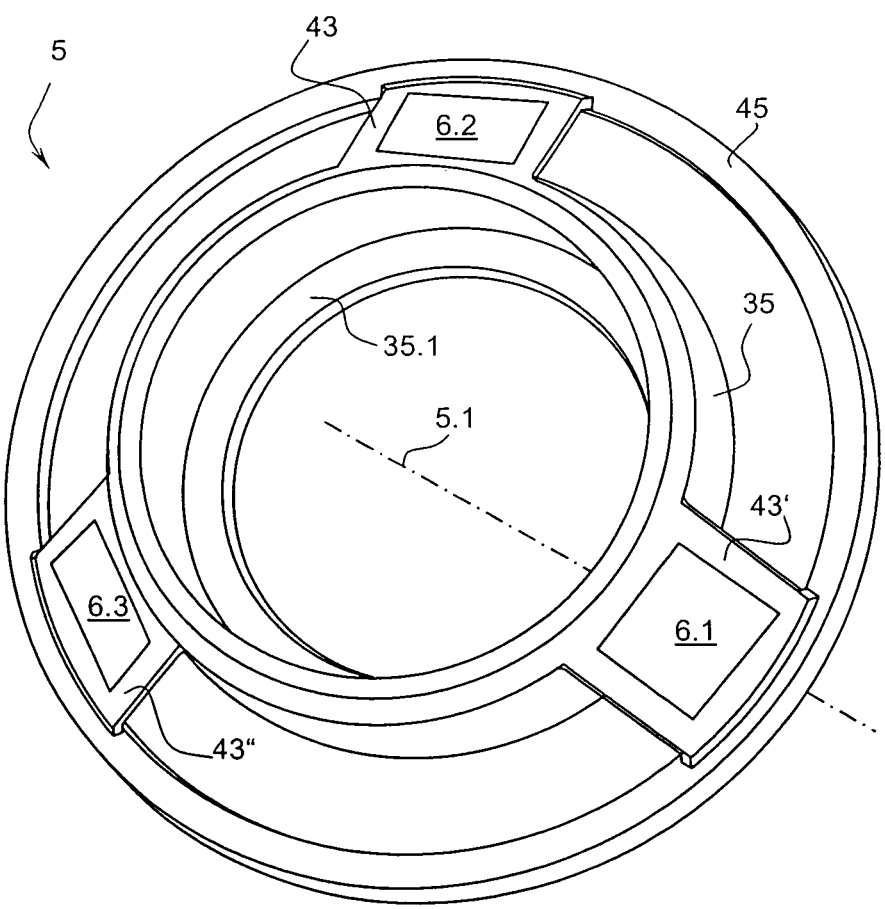
FIG. 4 is a schematic illustration of the combined axial/radial force detector.

The force sensor for sensing axial and radial forces shown in FIG. 4 is composed of a circular bearing 45 and a circular carrier 35 which are interconnected by three bracing members 43 to 43". The diameter of the bearing 45 is larger than the diameter of the carrier 35, the diameter difference being bridged by the bracing members 43 to 43". The diameter of the carrier 35 corresponds to the diameter of the race ring 7.1 of the rotary bearing 7 of spindle 2 for the purpose of mounting the race ring 7.1. The diameter of the bearing 45 corresponds to the diameter of the bearing housing 1.2 for the purpose of mounting it inside the bearing housing 1.2.

Furthermore, the force sensor 5 or the carrier 35 comprises an inner frontal race ring 35.1 at its end, via which a machining force absorbed by the outer race ring 7.1 and transferred through the carrier 35 to the bracing members 43 to 43", whence it passes through the bearing 45 to the bearing housing 1.2 (not shown).

A sensor element 6.1 to 6.3, having substantially the same basic rectangular shape, is disposed on the respective bracing members 43 to 43". Other forms corresponding to the machining force to be sensed are also provided for. When force is introduced into the spindle, the bracing members are deformed as dictated by the axial and radial forces.

The three bracing members 43 to 43" are distributed along the circumference offset from each other by 120° relative to the center axis 5.1. As shown in FIG. 6, each of the bracing members 43 to 43" encloses an angle α with the center axis 5.1 or in other words it is disposed at an angle α to the center axis 5.1.

The tool spindle 2 shown in FIG. 5 has a chuck system 2.4 for holding a tool 2.9. A motor, not shown, drives the spindle via a clutch 2.6. The motor shaft may be the tool spindle itself. The spindles 2 shown in FIGS. 4 and 6 each have a front rotary bearing 7 and a rear rotary bearing 8. Each of these bearings consists of an outer race ring 7.1, 8.1 and an inner race ring 8.2 (the inner-race ring 7.2 of the front rotary bearing 7 is not shown). Between the inner and outer race rings 7.1 to 8.2 there are provided, in each case, rolling members (not shown). The outer race ring 8.1 of the rear rotary bearing 8 bears against the force sensor 5 or against the bracing member 25.1. The force sensor 5 bears via the bracing members 15.3 against a holding ring 2.7, which, for the purpose of biasing the bearing system of the tool spindle, is affixed or screwed to the bearing housing 1.2 (not shown) of the machining apparatus 1. The front rotary bearing 7 is also mounted inside the bearing housing via the outer race ring 7.1. The suspension of the tool spindle 2 is sufficiently loose to enable sensing of the axial force, which can thus be detected by the force sensor 5 within the degree of freedom provided in the axial direction. Each of the sensor members 6.1 to 6.3 of the force sensor 5 is electrically connected via a lead 6.7.

On a front side face of the front rotary bearing 7 an undulated spring 2.3 is provided by means of which the rotary bearing 7, and therefore the tool spindle 2, the rotary bearing 8, and the force sensor can be spring-biased against the holding ring 2.7 affixed in the bearing housing 1.2.

The exemplary embodiment shown in FIG. 6 corresponds in principle to the variant shown in FIG. 5. In this case, as opposed to the exemplary embodiment shown in FIG. 5, the front rotary bearing 7 is connected via the force sensor 5 of FIG. 3 to the bearing housing 1.2 (not shown). The force sensor 5 is held by the carrier 35 on the outer race ring 7.1 of the front rotary bearing 7. The force sensor 5 is mounted on bearing 45 in the bearing housing 1.2 (not shown). Accordingly, the outer race ring 8.1 of the rear rotary bearing 8 is mounted in the bearing housing 1.2 (not shown). In this case, driving is accomplished via the clutch 2.6 and a motor (not shown) or via a motor with the tool spindle as the motor shaft. Each of the sensor members 6.1 to 6.3 is electrically connected via the respective lead 6.7, 6.7' and serves the purpose of detecting the radial and axial forces on the front bearing.

According to the exemplary embodiment shown in FIG. 7, the motor, consisting of a stator 9.1, an actor 9.2, and a lamination stack 9.3, is integrated in the spindle 2 or in its bearing housing 1.2. For this purpose, the actor or rotor 9.2 of the spindle 2 is constructed in the form of a permanent magnet, while the stator is in the form of a coil 9.1 and the lamination stack 9.3 are located on the housing side in the region of the spindle holder 1.3.

The front rotary bearing, consisting of an outer race 7.1 and an inner race 7.2, and a first spacing ring 4.1, the permanent magnet 9.2, a second spacing ring 4.2, and the rear rotary bearing 8, consisting of an outer race 8.1 and an inner race 8.2, are disposed on the tool spindle 2 or its shaft. The axial cutting forces absorbed by the spindle and the tool (not shown), are further transmitted, as shown in FIG. 5, through the outer race 8.2 to the force sensor 5 of FIGS. 2 and 4 and through its bracing members 15.3 to the holding ring and housing lid 2.7. An axial bias is provided by the spring 2.3, which is adjustable via the holding ring or via the housing lid 2.7.

The pin 25.5 engages a recess 1.4 of the bearing housing 1.2 and secures it against rotation.

For the purpose of changing the tool, the spindle holder 1.3 together with the bearing housing 1.2 and spindle 2 with its rotary bearing 7.8 can be removed from the dental machining apparatus or from a control unit holder (not shown) provided on the machine side to ensure movement in the X and Y directions.

Figure 8:
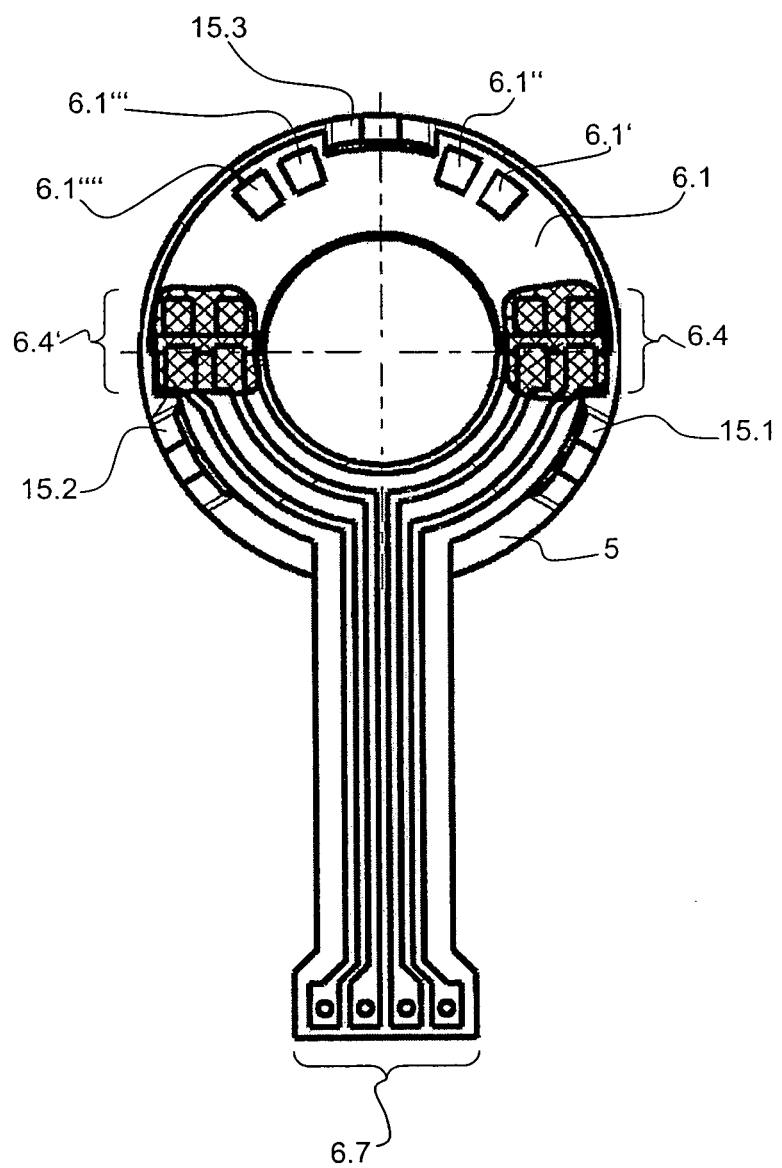
FIG. 8 shows an axial force sensor as in FIG. 3 with a strain-gage full bridge.

The axial force sensor 5 according to FIG. 2 is equipped, as shown in FIG. 8, on its first side 15 with a strain gage full bridge 6.1. The strain-gage full bridge 6.1 has four resistance meanders 6.11-6.11''', which are wired as a Wheatstone bridge. The resistance meanders 6.11-6.11''' are disposed in pairs to the left and right of the bracing members 15.2. The arc angle is about 60°, so that the pairs lie in the region of deformation of the disk of the force sensor, ie, between the bracing members. The strain-gage full bridge 6.1 is contacted by a lead 6.7 designed as a contact band. The lead 6.7 is in each case electrically connected to the strain gage full bridge by a solder joint 6.4, 6.4'.

LIST OF REFERENCE NUMERALS OR CHARACTERS

1. dental machining apparatus
1.1 machining chamber
1.2 bearing housing
1.3 spindel holder
1.4 recess
2 tool spindle
2' tool spindle
2.3 undulated spring
2.4 chuck system
2.5 tool
2.6 clutch
2.7 holding ring, housing lid
2.8 axis of rotation
2.9 tool
3 blank, workpiece
3.1 workpiece holder
4.1 spacing ring
4.2 spacing ring
5 force sensor, circular disk
5.1 center axis
15 flat face
15.1 bracing member
15.2 bracing member
15.3 bracing member
15.1' bracing member
15.2' bracing member
15.3' bracing member
25 flat face
25.1 bracing member
25.2 bracing member
25.3 bracing member
25.5 anti-rotation element, pin
35 annular carrier
35.1 stop limit surface on flat face
43 bracing member
43' bracing member
43" bracing member
45 annular bearing
6.1 sensor element, strain gage, strain gage full bridge
6.11 resistance meander
6.11' resistance meander
6.11" resistance meander
6.11''' resistance meander
6.2 sensor element, strain gage, strain gage full bridge
6.3 sensor element, strain gage, strain gage full bridge
6.4 solder joint
6.7 connecting lead
6.7' connecting lead
7 front rotary bearing
7.1 outer race ring, front bearing
7.2 inner race ring, front bearing
8 rear rotary bearing
8.1 outer race ring, rear bearing
8.2 inner race ring, rear bearing 9.1 stator, coil
9.2 actor, permanent magnet, rotor
9.3 lamination stack
α angle
X direction
Y direction
Z direction

The invention claimed is:

1. A dental machining apparatus comprising:
a tool spindle that has an axis of rotation;
a bearing housing in which the tool spindle is disposed;
a force sensor disposed between the tool spindle and the bearing housing that detects a machining force acting on the tool spindle, the force sensor being in the form of a single circular disk having a first flat face, a second flat face, a plurality of first bracing members regularly distributed on the first flat face, and a plurality of second bracing members regularly distributed on the second flat face;
a rotary bearing disposed between the tool spindle and the bearing housing;
a holding ring affixed to an end portion of the bearing housing; and
a spring that axially biases the force sensor against the holding ring,
wherein the number of first bracing members is the same as the number of second bracing members, and
wherein sensor elements are disposed on the single circular disk between adjacent first bracing members.

2. The dental machining apparatus according to claim 1, wherein at least one sensor element includes a bridge circuit or a piezo element, wherein the bridge circuit is formed as a strain-gage element.

3. The dental machining apparatus according to claim 1, wherein the force sensor is an axial force sensor and the single circular disk has at least a center axis,
wherein the first flat face and the second flat face oppose one another, and
wherein the rotary bearing bears against the force sensor, the force sensor bears against the holding ring, and the holding ring bears against the bearing housing in an axial direction relative to the axis of rotation of the tool spindle.

4. The dental machining apparatus according to claim 3, wherein each of the first bracing members is equidistantly offset in a circumferential direction from adjacent second bracing members, and a load on the first and second bracing members in the axial direction causes a bending load on the single circular disk.

5. The dental machining apparatus according to claim 4, wherein each of the first and second bracing members has a semicircular, an arcuate, or a trapezoidal shape.

6. The dental machining apparatus according to claim 4, wherein each of the first and second bracing members has a contact surface oriented in the axial direction and forms a flat or a pointed contact surface.

7. The dental machining apparatus according to claim 4, wherein at least three of the first bracing members are disposed on the first flat face and at least three of the second bracing members are disposed on the second flat face.

8. The dental machining apparatus according to claim 4, wherein the rotary bearing includes a race ring, wherein at least the first bracing members of the first flat face bear against the race ring.

9. The dental machining apparatus according to claim 4, wherein at least the second bracing members on the second flat face bear against the holding ring.

10. The dental machining apparatus according to claim 1, wherein a recess is formed in the bearing housing, and wherein the force sensor includes an anti-rotation element that engages the recess formed in the bearing housing.

11. The dental machining apparatus according to claim 1, wherein the rotary bearing includes an inner race ring and an outer race ring, and wherein the inner race ring bears against the tool spindle and the outer race ring bears against the bearing housing and the holding ring.

12. The dental machining apparatus according to claim 1, wherein the spring is disposed in a front end portion of the bearing housing and the holding ring is disposed in a rear end portion of the bearing housing.

13. The dental machining apparatus according to claim 1, wherein the spring provides an axial bias that is adjustable via the holding ring.

14. The dental machining apparatus according to claim 1, wherein the holding ring is screwed to the bearing housing.

15. The dental machining apparatus according to claim 1, wherein the first bracing members on the first flat face of the force sensor are offset from the second bracing members on the second flat face of the force sensor.

16. The dental machining apparatus according to claim 15, wherein the rotary bearing includes an outer race ring and the force sensor bears against the outer race ring directly or via the bracing members.

17. A dental machining apparatus comprising:
a tool spindle that has an axis of rotation;
a bearing housing in which the tool spindle is disposed;
a rotary bearing disposed between the tool spindle and the bearing housing;
a force sensor disposed between the tool spindle and the bearing housing that detects a machining force acting on the tool spindle, the force sensor including:
an annular carrier disposed around the tool spindle, the annular carrier having a center axis,
a coaxial annular bearing, different from the rotary bearing, disposed in the bearing housing, and
a plurality of sensor elements;
a holding ring affixed to an end portion of the bearing housing; and
a spring that axially biases the force sensor against the holding ring,
wherein the annular carrier and the coaxial annular bearing are interconnected by a plurality of bracing members, each bracing member including at least one of the plurality of sensor elements, and
wherein a load on the annular carrier in radial and axial directions deforms one or more of the bracing members.

18. The dental machining apparatus according to claim 17, wherein three of the bracing members are distributed uniformly along a circumference of the annular carrier.

19. The dental machining apparatus according to claim 17, wherein each bracing member is flat and has a rectangular cross-section.

20. The dental machining apparatus according to claim 17, wherein each of the bracing members forms an angle with the center axis between 0° and 90°.

21. The dental machining apparatus according to claim 17, wherein the rotary bearing includes a race ring, and the coaxial annular bearing bears against the race ring with a friction fit or a form fit and the annular carrier bears against the bearing housing with a friction fit or a form fit.

22. The dental machining apparatus according to claim 20, wherein the angle is between 30° and 60°.

* * * * *